United States Patent [19]

Urry et al.

[11] Patent Number: 4,605,413

[45] Date of Patent: Aug. 12, 1986

[54] STIMULATION OF CHEMOTAXIS BY CHEMOTACTIC PEPTIDES

[75] Inventors: Dan W. Urry, Birmingham, Ala.; Robert M. Senior, Clayton, Mo.

[73] Assignee: The University of Alabama at Birmingham, Birmingham, Ala.

[21] Appl. No.: 533,670

[22] Filed: Sep. 19, 1983

[51] Int. Cl.$^4$ .......................... A61F 2/02; A01N 1/02; A01N 25/00; A61K 9/38
[52] U.S. Cl. ............................... 623/11; 427/2; 424/36; 623/66
[58] Field of Search ................... 3/1, 1.4, 1.9; 424/36; 427/2; 106/124

[56] References Cited

U.S. PATENT DOCUMENTS 4,132,746  1/1979  Urry et al. ................................. 3/1.9
4,273,873  6/1981  Sugitachi et al. ........................... 3/1

OTHER PUBLICATIONS

PMR & Con. Engy. Cal. Rep. Pep. Trop., Renugopalakrishman et al.; Biochimica et Biophysica Arta; 536 (1979), pp. 421–428.

Mol. Med. for Elastin Stru. & Fun., Gray et al.; Nature; vol. 246; Dec. 1973, pp. 461–466.

*Primary Examiner*—Richard J. Apley
*Assistant Examiner*—Gregory Beaucage
*Attorney, Agent, or Firm*—Oblon, Fisher, Spivak, McClelland & Maier

[57] ABSTRACT

A method of stimulating chemotaxis toward a prosthetic device is disclosed, which method comprises incorporating a chemotactic peptide of the formula $$B^1\text{-}X\text{-}(APGVGV)_n\text{-}Y\text{-}B^2$$

wherein
A is a peptide-forming residue of L-alanine;
P is a peptide-forming residue of L-proline;
G is a peptide-forming residue of glycine;
V is a peptide-forming residue of L-valine;
$B^1$ is H or a biocompatible N-terminal group;
$B^2$ is OH, $OB^3$ where $B^3$ is a non-toxic metal ion, or a biocompatible C-terminal group;
X is PGVGV, GVGV, VGV, GV, V, or a covalent bond;
Y is APGVG, APGV, APG, AP, A, or a covalent bond; and
n is an integer from 1 to 100;

into a surface of the prosthetic device. Prosthetic devices which have the property of enhancing invasion of elastic fiber synthesizing fibroblasts as a result of the chemotactic peptide are also disclosed.

11 Claims, 4 Drawing Figures

STIMULATION OF CHEMOTAXIS BY CHEMOTACTIC PEPTIDES

BACKGROUND OF THE INVENTION

This work was supported in part by grants from the National Institutes of Health.

1. Field of the Invention

This invention relates to stimulation of chemotaxis, particularly in relation to prosthetic devices.

2. Description of the Prior Art

Replacement of a blood vessel by a prosthetic device is an important and common practice in modern vascular surgery. Although some use is made of veins or arteries taken from other portions of a patient's body, most of such prosthetic devices are prepared from artificial materials that can be prepared in a variety of sizes and stored in a sterile state ready for use.

There are several essential properties of cardiovascular prosthetic materials, among which are the following:
1. Retardation of thrombosis and thromboembolism (antithrombogenic);
2. Minimal harm to blood cells and minimal blood cell adhesion;
3. Long life as prosthetic inserts; and
4. High compliance with the physical and chemical properties of natural blood vessel such as similar elastic modulus and tensile strength.

Another useful property would be a chemotaxis that induced rapid endothelialization and invasion of connective tissue cells for vascular wall reconstruction in a manner such that the prosthesis would be slowly replaced by and/or integrated into newly synthesized internal elastic lamina. None of the materials presently being used can fulfill all of these requirements.

The most commonly used fabric for blood vessel prosthesis is made from Dacron (Trademark, Dupont), a synthetic polyester fiber made from polyethylene terephthalate. Dacron has been used in several weaves and in combination with other materials. An example of a frequently used material is the DeBakey Elastic Dacron fabric manufactured by USCI, a division of C. R. Bard, Inc. (Cat. No. 007830). Other commonly used materials are felted polyurethane and polytetrafluoroethylene (Berkowitz et al, Surgery, 72, 221 (1972); Wagner et al, J. Surg. Res., 1, 53 (1956); Goldfarb et al, Trans. Am. Soc. Art. Int. Org., XXIII, 268 (1977)). No chemotactic substance is normally used with these materials.

Another recent development in prosthetic devices is artificial skin of the type disclosed in Yannas and Burke, J. Biomed. Mat. Res., 14, 65–81 (1980). The artificial skin is a collagen/glycosaminoglycan (GAG) composite and had been successfully tested as full-thickness skin wound replacements. Such membranes have effectively protected wounds from infection and fluid loss for long periods of time without rejection and without requiring change or other invasive manipulation. Appropriately designed artificial skin of this type has retarded wound contraction, and the artificial skin has been replaced, at least in part, by newly synthesized connective tissue. Additional disclosure of this artificial skin is found in Yannas et al, ibid, 107–131 (1980), and Dagalakis et al, ibid, 511–528 (1980). No chemotactic substance is normally used with these materials.

One chemotactic material that might be useful in enhancing invasion of fibroblasts into such prosthetic devices is platelet-derived growth factor (PDGF), a potent fibroblast chemo-attractant. Unfortunately, PDGF cannot be synthesized and must be obtained from platelets, making the utilization of such a material on a wide scale impractical. Accordingly, there remains a need for an artificial and easily synthesized chemotactic material capable of attracting fibroblasts into prosthetic devices and thereby enhancing the incorporation of such devices into the regenerating natural tissue.

SUMMARY OF THE INVENTION

Accordingly, it is an object of this invention to provide an artificial material having chemotactic properties towards fibroblasts.

It is a further object of this invention to provide a prosthetic device which is readily incorporated into regenerating tissue, such as skin or blood vessel walls.

These and other objects of the invention as will hereinafter become more readily apparent have been accomplished by providing a method of stimulating chemotaxis, which comprises: incorporating a chemotactic peptide of the formula

$$B^1-X-(APGVGV)_n-Y-B^2$$

wherein
- A is a peptide-forming residue of L-alanine;
- P is a peptide-forming residue of L-proline;
- G is a peptide-forming residue of glycine;
- V is a peptide-forming residue of L-valine;
- $B^1$ is H or a biocompatible N-terminal group;
- $B^2$ is OH, $OB^3$ where $B^3$ is a non-toxic metal ion, or a biocompatible C-terminal group;
- X is PGVGV, GVGV, VGV, GV, V, or a covalent bond;
- Y is APGVG, APGV, APG, AP, A, or a covalent bond; and
- n is an integer from 1 to 100; into a surface of a prosthetic device in an amount sufficient to increase chemotaxis towards said surface.

This invention also comprises chemotactic surfaces and prosthetic devices prepared according to the method set forth above.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings wherein.

DESCRIPTION OF THE PREFERRED EMBODIMENTS

Figure 1:
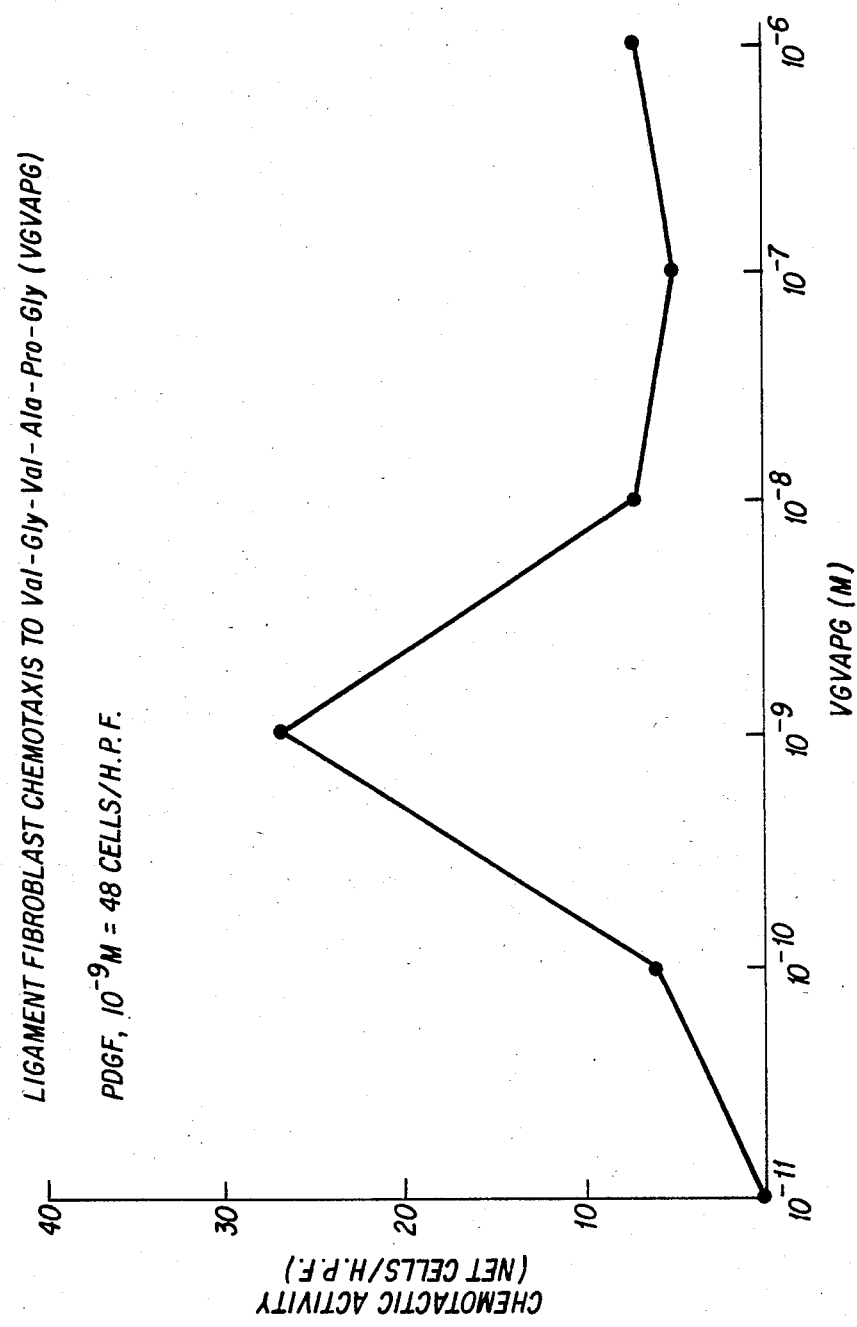
FIG. 1 is a graph of the chemotactic dose response of fibroblasts to VGVAPG.

The present invention arose as the result of investigations into the structure of elastic fibers present in blood vessel walls and other elastic materials, such as ligaments, present in humans and animals. The central portion of the elastic fibers of vascular wall, skin, lung and ligament is derived from a single protein called tropoelastin. Polypeptide sequences of tropoelastin from vascular wall have been shown by Sandberg and colleagues to to contain a repeat hexapeptide (Ala—Pro—Gly—Val—Gly—Val)$_n$, a repeat pentapeptide (Val—Pro—Gly—Val—Gly)$_n$, and a repeat tetrapeptide (Val—Pro—Gly—Gly)$_n$, where Ala, Pro, Val and Gly respectively represent alanine, proline, valine and glycine amino acid residues. (Peptide representations in this application conform to the standard practice of writing the NH$_2$-terminal amino acid residue at the left of the formula and the CO$_2$H-terminal amino acid residue at the right). A high polymer of the hexapeptide has been synthesized, whereby it forms cellophane-like sheets. The hexapeptide has therefore been thought to fill a structural role in the natural material.

However, recent investigations have indicated that this hexapeptide and permutations of this sequence are chemotactic for fibroblasts which synthesize elastic fiber precursor protein in biological systems. As a result of this discovery and related investigations into the various permutations of the natural material, it is expected that enhanced invasion of elastic-fiber-synthesizing fibroblasts will occur when a prosthetic device, designed for incorporation into regenerating tissue, is treated by incorporating a chemotactic peptide of the formula

$$B^1—X—(APGVG)_n—Y—B^2$$

wherein
- A is a peptide-forming residue of L-alanine;
- P is a peptide-forming residue of L-proline;
- G is a peptide-forming residue of glycine;
- V is a peptide-forming residue of L-valine;
- $B^1$ is H or a biocompatible N-terminal group;
- $B^2$ is OH, OB$^3$ where B$^3$ is a non-toxic metal ion, or a biocompatible C-terminal group;
- X is PGVGV, GVGV, VGV, GV, V, or a covalent bond;
- Y is APGVG, APGV, APG, AP, A, or a covalent bond; and
- n is an integer from 1 to 100; into a surface of the prosthetic device. In this way the surface of the prosthetic device becomes the source of a concentration gradient of the chemotactic peptide.

The isolated hexamers, such as H—VGVAPG—OH, and polyhexapeptides have the chemotactic property, although in varying amounts. The hexapeptide H—VGVAPG—OH is the most chemotactic of the isolated hexapeptides, although chemotactic activity is also seen for the other permutations; i.e., H—GVAPGV—OH, H—VAPGVG—OH, H—APGVGV—OH, H—PGVGVA—OH, AND H—GVGVAP—OH. When a polyhexapeptide is present, the compound (perhaps in the form of fragments derived therefrom by in vivo enzymatic action) is chemotactic regardless of the value of n. However, for ease of handling, values of n of no more than 100 are preferred since higher molecular weight compounds have limited solubility and difficult to handle. Preferred are values of n from 1 to 10, with values of about 5 being most preferred.

It will be noted that polyhexapeptides can be synthesized using any of the hexapeptide "monomers" listed above. Thus, polyhexapeptides generally will have the structure B$^1$-(repeating unit)$_n$-B$^2$ where B$^1$ and B$^2$ represent end groups which are discussed later. The repeating unit can be any of the permutations of the hexamer listed above. In fact, if the chemotactic peptide is not synthesized from hexapeptide "monomers" but rather is synthesized by sequential adding of amino acids to a growing peptide (such as in an automatic peptide synthesizer) the designation of a repeating unit is somewhat arbitrary. For example, the peptide H—VAPGV-GVAPGVGVAPGVGVAPGVGVA—OH can be considered to consist of any of the following repeating units and end groups: H—(VAPGVG)$_4$—VA—OH, H—V—(APGVGV)$_4$—A—OH, H—VA—(PGVGVA)$_4$—OH, H—VAP—(GVGVAP)$_3$—GV-GVA—OH, H—VAPG—(VGVAPG)$_3$—VG-VA—OH, or H—VAPGV—(GVAPGV)$_3$GVA—OH.

Synthesis of the chemotactic peptide is straight-forward and easily accomplished by a protein chemist. The resulting peptides generally have the structure B$^1$—(repeating unit)$_n$—B$^1$ where B$^2$ and B$^2$ represent any chemically compatible end group on the amino and carboxyl ends of the molecule, respectively, and n is an integer from 1 to about 100. When B$^1$ is H, B$^2$ is OH, and n=1, the compound is the hexapeptide itself. When n is greater than 1, the compound is a polyhexapeptide (often referred to herein as a polypeptide). It is possible that one or more amino acid residue or segment of amino acid residues not present in the normal polyhexapeptide sequence may be interspersed within a polyhexapeptide chain so long as the chemotactic character of the resulting molecule is not completely disrupted. As clearly indicated by the formula and by the following discussion, the invention encompasses incorporation of a hexamer or polyhexapeptide into a larger peptide chain in which B$^1$ and B$^2$ represent the remainder of the larger peptide chain.

Other examples of terminal B$^1$ and B$^2$ end groups include portions of the repeating peptide units themselves with free amino or carboxylic acid groups or salts thereof, free amino or carboxylic acid groups or salts (especially alkali metal salts), and peptide or amino acid units that have retained a blocking group that was present during synthesis of the polypeptide or that have a biocompatible group added after formation of the polypeptide. Examples of blocking groups include t-butyloxycarbonyl, formyl, and acetyl for the amino end of the molecule and esters, such as methyl esters, as well as amides, such as the amides of ammonia and methyl amine, for the acid end of the molecule. The end groups are not critical and can be any organic or inorganic group that does not destroy the chemotactic properties of the polypeptide or confer bio-incompatibility to the molecule as a whole. The term biologically compatible as used in this application means that the component in question will not harm the organism in which it is implanted to such a degree that implantation is as harmful as or more harmful than the needed prosthetic device.

Methods of preparing polypeptide polymers have been disclosed in Rapaka and Urry, *Int. J. Peptide Protein Res.*, 11, 97 (1978), Urry et al, *Biochemistry*, 13, 609 (1974), and Urry et al, *J. Mol. Biol.*, 96, 101 (1975), which are herein incorporated by reference. The synthesis of these peptides is straightforward and can be easily modified to any of the peptides disclosed herein. The following summary, which is not to be considered limiting, is an example of one general method of synthesizing the polypeptides.

The first step in the formation of a polyhexapeptide of the invention usually is synthesis of a hexapeptide monomer. Any of the classical methods of producing peptide molecules may be used in synthesizing the building blocks of the polymers of the present invention. For example, synthesis can be carried out by classical solution techniques starting from the C-terminal amino acid as benzyl (Bzl) ester p-tosylate. Each successive amino acid is then coupled to the growing peptide chain by means of its water-soluble carbodiimide and 1-hydroxybenzotriazole. A typically used carbodiimide is 1-(3-dimethylaminopropyl)-3-ethylcarbodiimide hydrochloride (EDCI). During the coupling reaction the amino group is protected. The protecting group is then removed after condensation has taken place. A suitable protecting group is tert-butyloxycarbonyl (Boc), which can easily be removed by trifluoroacetic acid.

The first product obtained in the synthesis of the hexapeptide monomer is a protected hexapeptide, such as Boc—L.Val—L.Ala—L.Pro—Gly—L.Val—Gly—OBzl. This protected monomer is converted into the reactive monomer by, for example, replacement of the benzyl ester with the p-nitrophenyl ester, for example by effectively exchanging with p-nitrophenyl trifluoroacetate, and removal of the Boc protecting group. The resulting reactive monomer is polymerized, in the presence of a base such as triethylamine as necessary, to give the polypeptide. A blocking group, such as H—Val—OMe may be added at the conclusion of the polymerization reaction to convert the remaining reactive p-nitrophenyl esters to non-reactive terminal groups if desired.

When a modified chemical structure is desired, as, for example, when chemical cross-linking between two chains of polyhexapeptide or between a polyhexapeptide chain and a peptide-forming part of the structure of a prosthetic device will be carried out, side-group-blocked lysine or glutamic acid (or another amino acid with a protected side group capable of forming a cross-link after the protecting group is removed) may be utilized in place of one of the normal amino acids that is present in the polypeptide chain. A synthesis of a chemically cross-linked polypentapeptide of similar structure is disclosed in U.S. Pat. No. 4,187,852, which is herein incorporated by reference.

It is not necessary for the chemotactic peptide of the invention to be covalently attached to the surface toward which chemotaxis is being stimulated. It is sufficient that the peptide be present at the surface. Therefore, the phrase "incorporating into a surface" as used in this application encompasses all methods of applying a chemotactic peptide of this invention to a surface, whether that application results in chemical bonding or not. For example, solutions or suspensions containing the peptide can be painted on the surface of a prosthetic device or a device can be submerged in a solution of the chemotactic peptide.

It is also possible to form covalent bonds between the chemotactic peptide and the prosthetic device. For example, during the synthesis of a chemotactic peptide as described above, various intermediates are produced which have reactive carboxy or amino terminals. Many of the prosthetic devices which are intended for incorporation into regenerating tissue are prepared from collagen or related materials and therefore contain free amino acid functional groups, such as amino or carboxylic acid groups. Peptide bonds can easily be formed between such functional groups in the prosthetic device and reactive intermediates such as those described above.

The type of prosthetic device which can be used in conjunction with the present invention is not limited, since the chemotactic property is related to the peptide and not to the prosthetic device itself. It is preferred, however, that the prosthetic device be one which is intended for incorporation into regenerating tissue, such as an artificial vein or artery or artificial skin. Publications which disclose various prosthetic devices useful for forming artificial skin or blood vessel walls are listed in the section of this application entitled *Background of the Invention*, and these publications are herein incorporated by reference. Two particularly preferred embodiments of the present invention involve using the chemotaxic polypeptide with a collagen/glycosaminoglycan composite material as an artificial skin, as described in U.S. Pat. No. 4,280,594, and with biocompatible artificial materials based on polypeptides as described in U.S. Pat. No. 4,187,852; U.S. patent application Ser. No. 308,091, filed Oct. 2, 1981; and U.S. patent application Ser. No. 452,801, filed Dec. 23, 1982, all of which are herein incorporated by reference. These are peptide-containing materials, and the chemotactic polypeptide may readily be attached by covalent bonding into such materials by the methods described above. However, as also previously indicated, covalent bonding is not necessary and indeed is not preferred since the chemotactic property is also exhibited when the chemotactic peptide is merely present on the surface or in the pores of a prosthetic material. Prosthetic devices having surfaces comprising other structural peptides are also preferred over prosthetic devices having other types of surfaces, although other types of surfaces, such as Dacron, and other synthetic fibers, are specifically included. Examples include natural materials such tendons or ligaments (for example, those transferred from one location to another within the same body) and synthetic or semi-synthetic materials. Semi-synthetic materials are those derived by manipulation of natural materials, such as collagen.

The amount of chemotactic peptide which is required for a particular prosthetic device can easily be determined by simple experimentation. Generally, quite low concentrations of the chemotactic peptide are required. For example, doping of a non-chemotactic surface to produce low concentrations of 0.1 nM to 100 nM of a chemotactic peptide at the surface will be sufficient. Generally, from $10^{-9}$ to $10^{-3}$ millimoles of hexamer or repeating unit of a polyhexapeptide per 100 cm$^2$ of surface is sufficient for this purpose. It is preferred to roduce a concentration of the chemotactic hexamer of from $10^{-9}$ to $10^{-7}$M within a distance of 1 millimeter of the surface.

Alternatively or additionally, a 2-component synthetic bioelastomer comprising the chemotactic peptide of this invention and the elastic polypentapeptide or polytetrapeptide of U.S. Pat. No. 4,187,852 would act as a chemotactic elastic biopolymer which could be utilized for a variety of purposes. It is also possible to use the chemotactic peptide of this invention in a system involving natural crosslinking of synthetic bioelastomers, as is described in U.S. patent application Ser. No. 533,524 by Urry filed on even date with the present application, which is herein incorporated by reference. That application discloses bioelastomers which are enzymatically cross-linked by lysyl oxidase.

The above disclosure generally describes the present invention. A more complete understanding can be obtained by reference to the following specific examples, which are provided herein for purposes of illustration only and are not intended to be limiting unless otherwise specified.

EXAMPLE

The chemotactic response of fibroblasts to a hexapeptide of the invention was measured using the techniques described in Senior et al, *J. Clin. Invest.*, 70, 614–618 (1982), which is herein incorporated by reference. Although the actual conditions used may vary slightly, the following generally describes the experimental conditions.

Chemotaxis was determined in a multi-blind well apparatus using a polycarbonate membrane with 8-μm pores on top of a cellulose nitrate membrane having 0.45-μm pores to separate each well into upper and lower compartments. The lower compartment was filled with 240 μl of solution to be assayed (or control medium) and then covered with the membranes. In the upper compartment was placed 350 μl of cell suspension containing $1.2 \times 10^5$ cells/ml.

After both compartments of the wells were filled, the chemotaxis apparatus was placed in a humidified incubator at 37° C. in an atmosphere of 5% $CO_2$–95% air for several hours. The apparatus was then disassembled, and each membrane pair was removed and stained with hematoxylin. Cell migration was determined under high dry magnification (×400) by counting the cells that had moved to the interface between the two membranes and those on the lower membrane. Several high power fields (H.P.F.) were counted for each membrane. Multiple determinations of each experiment were conducted, and the results pooled. Cell migration is expressed as the net number of cells per H.P.F.; i.e., the number of cells per H.P.F. minus the number of cells per H.P.F. that migrated in response to control medium.

The results of these experiments demonstrate the chemotactic character of the hexamer of the invention H—VGVAPG—OH. FIG. 1 shows in graphical form the chemotactic activity of VGVAPG at various concentrations. Response was seen at all concentrations tested higher than $10^{-11}$M with the greatest activity being at a concentration of $10^{-9}$M. Table 1 shows that the fibroblast response to VGVAPG is indeed chemotaxis and not simply stimulation of random movement since response occurs only when there is a concentration gradient of higher VGVAPG concentration in the lower compartment of the test well compared to the VGVAPG concentration in the upper compartment where the cells are first placed.

TABLE 1

| Fibroblast Migration to VAL—GLY—VAL—ALA—PRO—GLY | | | | |
|---|---|---|---|---|
| VGVAPG, (M), Lower Compartment | 0 | VGVAPG, (M), $10^{-10}$ | Upper Compartment $10^{-9}$ | $10^{-8}$ |
| 0 | (7) | 1 ± 0.6 | 0 ± 0.7 | −2 ± 0.5 |
| $10^{-10}$ | 4 ± 1.0* | 2 ± 0.7 | −3 ± 0.4 | 1 ± 1.0 |
| $10^{-9}$ | 15 ± 1.7 | 7 ± 1.3 | 0 ± 0.4 | 0 ± 0.6 |

TABLE 1-continued

| Fibroblast Migration to VAL—GLY—VAL—ALA—PRO—GLY | | | | |
|---|---|---|---|---|
| VGVAPG, (M), Lower Compartment | 0 | VGVAPG, (M), $10^{-10}$ | Upper Compartment $10^{-9}$ | $10^{-8}$ |
| $10^{-8}$ | 27 ± 1.7 | 13 ± 1.8 | 3 ± 0.6 | 1 ± 0.7 |

*Net Cells/HPF ± SEM, N = 15
Positive Control (PDGF, $10^{-9}$ M = 31 Cells/HPF)

Figure 2:
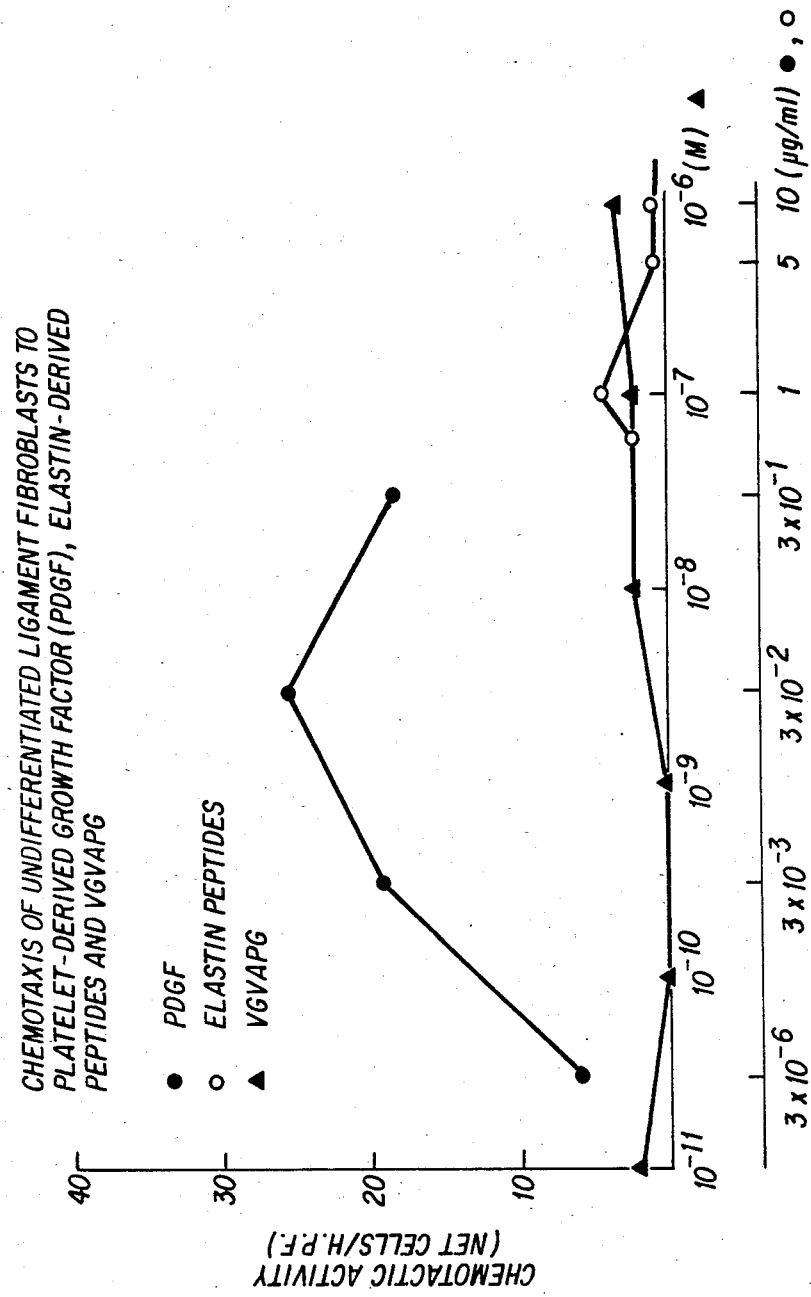
FIG. 2 is a graph comparing the response of immature fibroblasts to VGVAPG, to peptides derived from elastin, and to PDGF.
Figure 3:
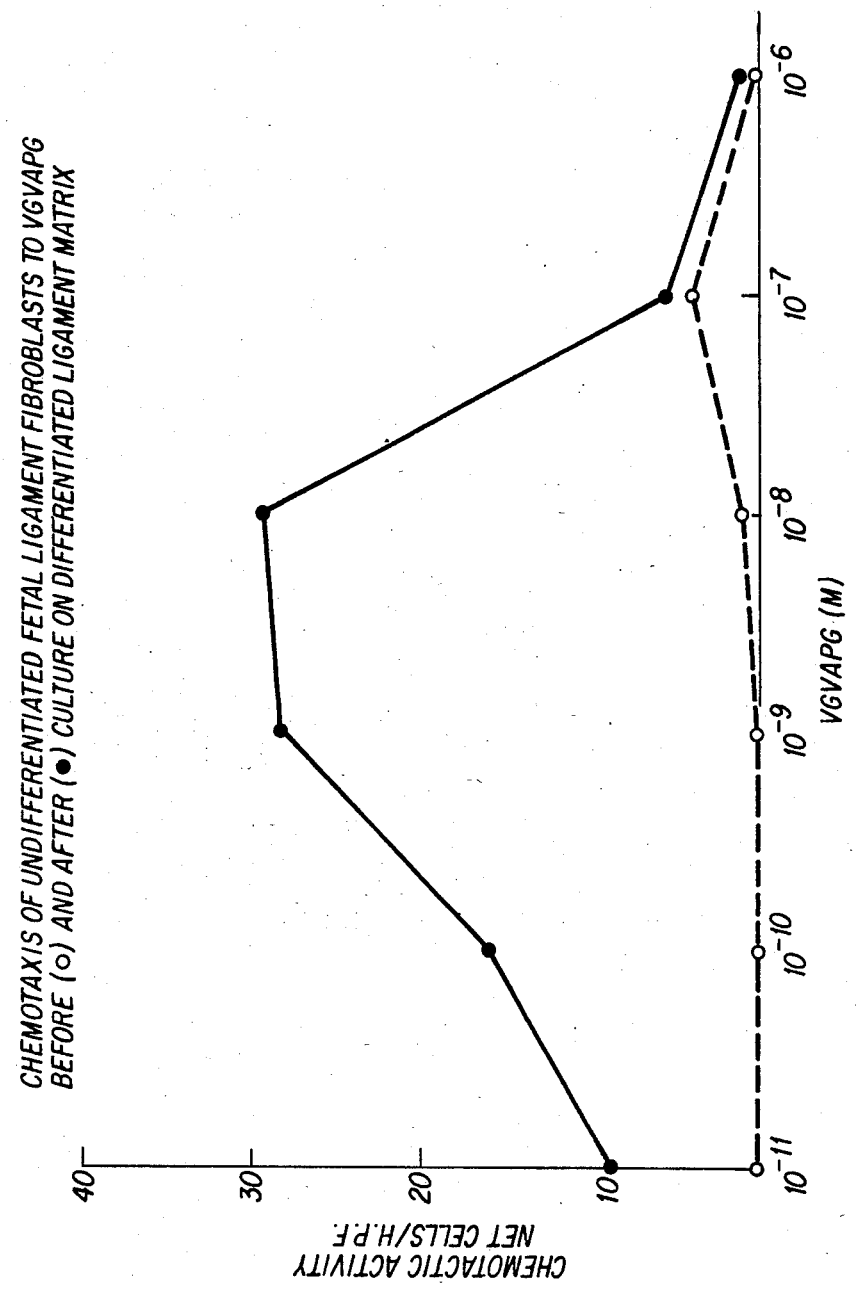
FIG. 3 is a graph comparing the response of fibroblasts to VGVAPG before and after they have been induced to differentiate.

FIG. 2 shows that young fibroblasts (not yet synthesizing elastin) do not migrate in response to either VGVAPG or peptide fragments derived from elastin, although they have the capacity to migrate as shown by their response to PDGF. However, the young fibroblasts will respond to VGVAPG after they have been induced to differentiate, as shown in FIG. 3.

Figure 4:
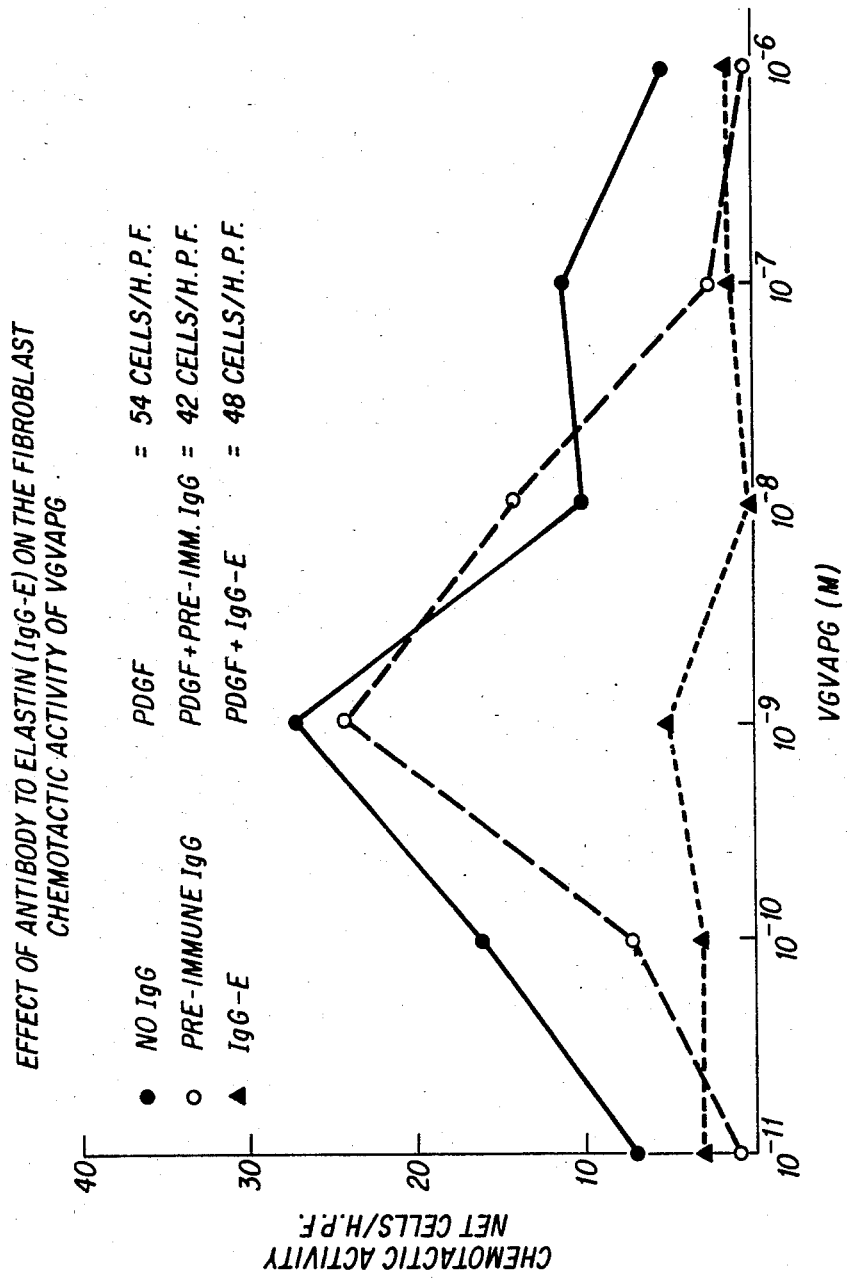
FIG. 4 is a graph comparing the response of fibroblasts to VGVAPG in the presence and absence of an antibody against elastin.

The specificity of the chemotactic response is shown by the data graphed in FIG. 4. A polyclonal antibody to elastin blocks the chemotactic activity of VGVAPG but has no effect on the chemotactic activity of PDGF.

Other indications of specificity are shown in the data presented in Table 2. Monocytes are desensitized the VGVAPG (i.e., they no longer show chemotaxis) after pre-exposing them to elastin-derived peptide fragments, presumably because the receptors are saturated or there is down regulation of the receptors. The effect appears to be specific since pre-exposure has no effect on response to totally unrelated chemo-attractants such as formylmethionylleucylphenylalanine (FMLP) or activity derived from the fifth component of complement (C5a).

TABLE 2

| DESENSITIZATION OF MONOCYTES TO ELASTIN PEPTIDES AND VGVAPG BY PRE-EXPOSURE TO ELASTIN PEPTIDES | | | |
|---|---|---|---|
| CHEMO-ATTRACTANT | CONTROL* | DESENSI-TIZED* | % CONTROL |
| C5A** | 102 | 102 | 100 |
| FMLP (M) | | | |
| $10^{-9}$ | 45 | 45 | 100 |
| $10^{-8}$ | 100 | 77 | 77 |
| ELASTIN PEPTIDES (μg/ml) | | | |
| 25 | 36 | −2 | 0 |
| 50 | 65 | −1 | 0 |
| 100 | 90 | 0 | 0 |
| VGVAPG (M) | | | |
| $10^{-9}$ | 42 | −2 | 0 |
| $10^{-8}$ | 70 | −4 | 0 |

*Cells per high power field (mean of 15)
**Concentration for maximum chemotaxis

The invention now being fully described, it will be apparent to one of ordinary skill in the art, that many changes and modifications can be made thereto without departing from the spirit or scope of the invention as set forth herein.

What is claimed as new and desired to be secured by Letters Patent of the United States is:

1. A prosthetic device wherein a surface of said device has a chemotactic peptide of the formula $B^1$—X—(APGVGV)—Y—$B^2$ wherein
A is a peptide-forming residue of L-alanine;
P is a peptide-forming residue of L-proline;

G is a peptide-forming residue of glycine;

V is a peptide-forming residue of L-valine;

$B^1$ is H or a biocompatible N-terminal group;

$B^2$ is OH, $OB^3$ where $B^3$ is a non-toxic metal ion, or a biocompatible C-terminal group;

X is PGVGV, GVGV, VGV, GV, V, or a covalent bond;

Y is APGVG, APGV, APG, AP, A, or a covalent bond; and n is an integer from 1 to 100; incorporated into said surface.

2. The device of claim 12, wherein n is from 1 to 10.

3. The device of claim 1, wherein n is about 5.

4. The device of claim 1, wherein n is 1.

5. The device of claim 1, wherein said peptide is H—VGVAPG—OH, H—GVAPGV—OH, H—VAPGVG—OH, H—APGVGV—OH, H—PGVGVA—OH, H—GVGVAP—OH, or a salt thereof.

6. The device of claim 1, wherein $B^1$ is H and $B^2$ is OH or $OB^3$ where $B^3$ is an alkali metal ion.

7. The device of claim 1, wherein said amount is from $10^{-9}$ to $10^{-3}$ millimoles of hexamer or repeating unit per 100 $cm^2$ of said surface.

8. The device claim 1, wherein said prosthetic device comprises a structural polypeptide.

9. The device of claim 1, wherein said chemotactic peptide is incorporated using non-covalent bonding between said chemotactic peptide and said surface.

10. The device of claim 1, wherein said chemotactic peptide is incorporated using covalent bonding between said chemotactic peptide and said surface.

11. The device of claim 10, wherein said surface comprises a structural peptide.

* * * * *